US009999780B2

(12) United States Patent
Weyh et al.

(10) Patent No.: US 9,999,780 B2
(45) Date of Patent: Jun. 19, 2018

(54) MAGNETIC STIMULATION HAVING A FREELY SELECTABLE PULSE SHAPE

(75) Inventors: Thomas Weyh, Munich (DE); Stefan M. Götz, Forstern (DE)

(73) Assignee: Technische Universitat Munchen, Munich (DE)

(*) Notice: Subject to any disclaimer, the term of this patent is extended or adjusted under 35 U.S.C. 154(b) by 851 days.

(21) Appl. No.: 13/521,434

(22) PCT Filed: Jan. 11, 2011

(86) PCT No.: PCT/EP2011/000081
§ 371 (c)(1),
(2), (4) Date: Oct. 11, 2012

(87) PCT Pub. No.: WO2011/083097
PCT Pub. Date: Jul. 14, 2011

(65) Prior Publication Data
US 2013/0030239 A1    Jan. 31, 2013

(30) Foreign Application Priority Data
Jan. 11, 2010 (DE) .................. 10 2010 004 307

(51) Int. Cl.
*A61N 2/00* (2006.01)
*A61N 2/02* (2006.01)
*H03K 17/13* (2006.01)

(52) U.S. Cl.
CPC .............. *A61N 2/006* (2013.01); *A61N 2/02* (2013.01); *H03K 17/136* (2013.01)

(58) Field of Classification Search
CPC .. A61N 1/40; A61N 1/36021; A61N 1/36025; A61N 2/00; A61N 2/004; A61N 2/006; A61N 2/02
See application file for complete search history.

(56) References Cited

U.S. PATENT DOCUMENTS

2003/0032852 A1* 2/2003 Perreault et al. ................ 600/9
2005/0033380 A1  2/2005 Tanner et al.
(Continued)

FOREIGN PATENT DOCUMENTS

DE    3524232 A1    1/1987
DE    101 030 31 A1    7/2002
(Continued)

OTHER PUBLICATIONS

Goetz, S.M. et al. "Analysis of a novel magnetic stimulation system: Magnetic harmonic multi-cycle stimulation (MHMS)," International Conference on Biomedical and Pharmaceutical Engineering, ICBPE, IEEE, Piscataway, NJ, USA, Dec. 2, 2009.
(Continued)

*Primary Examiner* — Charles A Marmor, II
*Assistant Examiner* — Carrie R Dorna
(74) *Attorney, Agent, or Firm* — Klarquist Sparkman LLP

(57) ABSTRACT

Device and method for generating brief strong current pulses in a coil for generating magnetic field pulses which according to the electromagnetic induction principle induce stimulation currents in the body tissue triggering an action potential of the nerve and/or muscle cells, where the coil is positionable close to the body tissue to be stimulated so that its magnetic field passes through the body tissue, and where the device comprises a power generating unit that can generate a freely selectable temporal course of the current through the coil during the current pulse. A method for determining an optimized temporal course of a brief strong current pulse through the coil, where the temporal course of the current pulse is calculated using a method which numerically simulates the electrical behavior of nerve and/or muscle cells and the coil and optimizes the course of the current pulse regarding at least one parameter, or which by means of stimulating the nerve and/or muscle cells with (Continued)

predetermined current pulses optimizes the temporal course of the current pulse regarding at least one parameter and therefrom determines essential parameters of nerve and/or muscle cells.

7 Claims, 10 Drawing Sheets

(56) References Cited

U.S. PATENT DOCUMENTS

| | | |
|---|---|---|
| 2007/0293916 A1* | 12/2007 | Peterchev .................... 607/61 |
| 2009/0018384 A1 | 1/2009 | Boyden et al. |
| 2010/0160713 A1* | 6/2010 | Cuppen ...................... 600/14 |

FOREIGN PATENT DOCUMENTS

| | | |
|---|---|---|
| DE | 10 2009 023 855 A1 | 12/2010 |
| EP | 0 958 844 A2 | 11/1999 |
| EP | 1 894 600 A1 | 3/2008 |
| WO | WO 99/59674 A1 | 11/1999 |
| WO | WO 2004/103173 A1 | 12/2004 |
| WO | WO2007/145838 A2 | 12/2007 |

OTHER PUBLICATIONS

Hiwaki, O. et al. "Nerve Excitation Properties in Magnetic Stimulation by Trapezoidal Magnetic Fields," IEEE Translation Journal on Magnetics in Japan, IEEE, Inc., New York, USA, May 1, 1994.
International Search Report from PCT/EP2011/000081, dated Apr. 11, 2011, 3 pp.

* cited by examiner

MAGNETIC STIMULATION HAVING A FREELY SELECTABLE PULSE SHAPE

CROSS REFERENCE TO RELATED APPLICATIONS

This is the U.S. National Stage of International Application No. PCT/EP2011/000081, filed Jan. 11, 2011, which was published in English under PCT Article 21(2), which in turn claims the benefit of German Application No. 10 2010 004 307.9, filed Jan. 11, 2010.

The present invention relates generally to a method and a device for stimulating nerve and muscle cells in the body tissue in accordance with the electromagnetic induction principle by means of brief strong magnetic field pulses being created by a coil. The invention further relates to electrical power circuits for generating freely selectable temporal courses of brief, strong current pulses through the coil to generate pulse-shaped magnetic fields for stimulating nerve and muscle cells.

BACKGROUND OF THE INVENTION

Generally, specific cells in the body tissue can be stimulated by electrical fields acting from the outside. Nerve or muscle cells can in particular be excited by depolarization of an axon or a bundle of fibers, respectively, stimulated by an external field, and the triggering of action potentials and the subsequent stimulus conduction resulting therefrom. This is done in that the electric fields cause electrical currents in the tissue, which in turn trigger action potentials in these cells. This type of triggering action potentials by an electrical field acting directly upon the axon is a non-physiological process: In nature, action potentials are generated in the cell body of the nerve cell itself, after signals coming in via the dendrites have been linked respectively.

The electric field acting from the outside must for triggering such an action potential reach a certain temporal course and a certain minimum strength. In particular, regarding the triggering of an action potential, different cell types also react differently to temporal courses and strengths of the fields acting from the outside. By way of example, sensory nerve fibers also being responsible for the transmission of pain signals, due to their smaller diameter require a higher field strength for depolarization (i.e. for triggering an action potential) than motor nerve fibers. At moderate stimulus intensities it is therefore possible to stimulate only the motor but not the sensory fibers and therefore to stimulate nerves virtually without pain.

The principle of magnetic induction can be used in particular for this type of stimulation. In this, a time-varying magnetic field generates an induced electric field. The time-varying magnetic field can be generated by a coil which has time-varying current passing through. This coil is located, for example, on the skin above the nerve tissue to be stimulated, so that the generated magnetic field can penetrate the tissue and, according to the induction principle, generate the currents in the tissue necessary for stimulation. In this, stimulation by the so-called inductive magnetic stimulation can occur contactless, since the magnetic field can penetrate body tissue without hindrance. The time-dependent magnetic fields are generated by brief current pulses having a duration of usually of 50-400 microseconds. The principle of inductive stimulation is based principally on a temporal change of the magnetic field. In this manner, only time-varying electric fields can also be created in the tissue. Therefore, no efficient single monophasic rectangular pulses having a direct (DC) component can for example be generated as they are used in the electrical stimulation.

An advantage of the inductive magnetic stimulation is that it is contactless, as the magnetic field of the coil also reaches the body tissue being at a certain distance from the coil. Therefore, nerve cells can be stimulated in a sterile manner. Another advantage is that the method, in contrast to electrical stimulation via electrodes, is almost completely painless, because contrary to electrical stimulation, no high current densities can arise at the locations of application of the electrodes. For these reasons, the method is also particularly suitable for stimulation of deeper-lying tissue structures (e.g. the cerebral cortex through the cranial bone) and for pain-free muscle stimulation e.g. in the field of rehabilitation.

Due to these advantages, the inductive magnetic stimulation was able to already prevail over electric stimulation in some fields or even open up new fields of application. The procedure is very common for application to the central and the peripheral nervous system.

Currently it is the only non-invasive procedure, with which, for example, certain brain areas can be selectively activated without any pain for the individual (i.e. triggering nerve action potentials or subliminal influencing of nerve cells in these regions) such that responses by nerve cells can be processed by the body just like, or at least very similar to, naturally occurring nerve impulses.

The inductive magnetic stimulation is used in fundamental research as a tool for joint examination together with functional magnetic resonance imaging. Selective excitation (and inhibition) of certain brain areas can be induced via pulses, the effects of which can in turn be examined by magnetic resonance imaging.

Furthermore, there are applications of inductive magnetic stimulation regarding peripheral motor nerves. In this, repetitive continuous stimulation with fast pulse sequences (10 to 50 pulses per second) is of great significance.

Applications for apparatuses used in high performance sports are known.

FIG. 1 shows a typical arrangement of the previous use of the inductive magnetic stimulation. The pulse source 110 generates a brief strong current pulse and conducts it to the coil 120. The coil 120 is positioned close to the body nerve tissue to be stimulated, so that the generated magnetic field can penetrate this tissue structure. The magnetic field generated by the coil induces an electric field in the body tissue, presently the upper arm 130, which stimulates nerve and muscle tissue via the resulting currents.

However, for the inductive magnetic stimulation, this detour through the magnetic field of the coil also causes important technical problems:

The required magnetic flux densities are in the range of about 1 Tesla, so that during the very brief magnetic stimulation pulse, extremely high electric power must be provided to the coil in order to generate the appropriate field energies. The required electrical power can reach values of several megawatts and the currents can reach several kilo amperes at voltages of several kilovolts. Therefore, the pulse sources are technically complex; furthermore the coil very quickly overheats due to the current heat losses, where it must presently be additionally considered that the coil may not reach too high temperatures as it is a component that can directly contact the body.

In order to nevertheless be able to provide respective currents and energies for this type of stimulation with a reasonable technical available effort, magnetic stimulation devices presently operate according to the principle of the resonant oscillating circuit in which a capacitor discharges its energy into the coil. The principle of generating powerful pulses for the coil is thus based on a continuous charge of the oscillating circuit capacitor via a charging device at relatively low power and the rapid discharge of the energy content of this capacitor to the coil for generating the brief strong magnetic field pulse.

FIG. 2 shows the basic circuit structure of an inductive stimulation device as used in the first devices in particular for contactless stimulation of cortical nerve structures through the intact cranial bone (R. Siebner, U. Ziemann, "Das TMS-Buch/The TMS-book", Springer publishing house, ISBN-13 978-3-540-71904-5). For this, the circuit uses a powerful damped electrical oscillation circuit (resonator) comprising a capacitor 220, a damping resistor 230, a diode 240, a thyristor 250 and the coil 260. The charging circuit 210 charges the capacitor 220 to a voltage of several thousand volts. The energy content of the capacitor amounts to several 100 joules. The thyristor 250 serves as a switch which during ignition connects the capacitor 220 with the magnetic coil 260 and thus lets the current flow in the coil begin.

FIG. 3 shows the temporal course of current and voltage in the coil according to the circuit of FIG. 2. Upon ignition of the thyristor, an initially sinusoidally increasing current flow develops, which generates a corresponding magnetic field increasing with time. This magnetic field in turn induces ring currents in the body tissues as a result of its change over time. The phase-shifted coil voltage has its first zero crossover exactly upon reaching the current peak value. Since from this point on, the coil voltage reverses its sign, the damping circuit comprising the resistor 230 and the diode 240 now becomes active, preventing further oscillation of the oscillating circuit. Therefore, the coil current, after reaching its peak value, slowly falls back to zero. The typical time period between the thyristor ignition and reaching the current peak value is about 50 to 150 microseconds. By means of this damping circuit, however, the entire pulse energy of the capacitor in the resistor 230 and in the coil conductors of the coil is transformed to heat.

This damping circuit being employed in the first devices, which dampens the oscillation from the first dropping current edge (after one quarter of the period duration), characterizes the so-called monophasic stimulation, as the coil current during the pulse only flows in one direction, i.e., does not change its sign. Since for these devices, the pulse energy of the magnetic field is completely lost with each pulse, these devices have particularly high energy consumption.

These first devices were therefore not suitable for so-called repetitive stimulation for which 10 to 50 pulses per second are required. Furthermore, also the size of the devices and their high price make it difficult to open new fields of application.

Therefore, the most important development goal for the devices for inductive magnetic stimulation lies in the reduction of energy consumption and heating of the coil (R. Siebner, U. Ziemann, "Das TMS-Buch", Springer publishing house, ISBN-13 978-3-540-71904-5). It was shown by experimental studies, that an undamped sinusoidal temporal course of the coil current and thus also of the magnetic field at the same amplitude shows an equivalent effect regarding nerve stimulation as the current profile of FIG. 3.

FIG. 4 shows the basic circuit configuration of another known stimulation device, as used in a later generation of devices. This device generates sinusoidal current or field pulses, respectively. Here as well, the charging circuit 210 charges the capacitor 220 to a voltage of several thousand volts. The thyristor 410 again serves as a switch which during ignition connects the capacitor 220 with the magnetic coil 260. In contrast to the monophasic stimulator circuit of FIG. 2, however, no damping circuit is used for this circuit, so that the oscillating circuit continues to oscillate even after the first zero crossover of the coil current.

FIG. 5 shows the temporal course of current and voltage in the coil according to the circuit of FIG. 4. Upon igniting the thyristor, a sinusoidally increasing current flow develops, which generates a corresponding magnetic field increasing with time. After half a sinusoidal oscillation, at time T/2, the current in the oscillating circuit changes its polarization. At this time, the diode 420 takes over conduction of the coil current until a full sinusoidal oscillation at time T is reached. A renewed reversal of the current direction and thus continued oscillation is prevented because the thyristor 410 is at this time T no longer conductive. Due to the reversal of the direction of current during a pulse at time T/2, this type of stimulation is generally referred to as biphasic magnetic stimulation.

It can be achieved by the circuit principle according to FIG. 4, that a large proportion of the field energy expended for the coil 260 can be returned to the capacitor 220 thus reducing the losses in both the pulse source as well as in the coil 260. The losses of the circuit of FIG. 4 mainly result via the ohmic resistances of the circuit components involved and their connection cables.

As, however, the current amplitude, required for successful stimulation, remains approximately unchanged compared with the devices with monophasic pulse shape, the necessary voltage and the energy content of the capacitor 220 remain nearly the same as with monophasic devices.

FIG. 6 shows a further development of the known circuits of inductive motors magnetic stimulators, as was used in a later generation of devices (R. Siebner, U. Ziemann, "Das TMS-Buch", Springer publishing house, ISBN 13978-3-540-71904-5) Here as well, the charging circuit 210 charges the capacitor 220 to a voltage of several thousand volts. The thyristor 610 again serves as a switch which during ignition connects the capacitor 220 with the magnetic coil 260.

FIG. 7 shows the temporal course of current and voltage in the coil according to the circuit of FIG. 6. Upon igniting the thyristor, a sinusoidally increasing current flow develops, which generates a corresponding magnetic field increasing with time. After half a sinusoidal oscillation, at time T/2, the current in the oscillating circuit reaches its first zero point. If at this point in time the second thyristor 620 is not ignited, reversal of the current direction is not possible, so that a continued oscillation is prevented already after half a wave. Ignition of the thyristor 620 at a later time generates a further half-wave pulse in the coil with reversed current and magnetic field direction. Alternatively, however, upon reaching the first current zero point, the second thyristor 620 can also be ignited directly so that a full sinusoidal oscillation is formed, similar to FIG. 5. In any case, also for this circuit, the field energy of the coil is to a large extent returned to the capacitor.

Depending on the choice of the end time of the pulse, it is therefore distinguished regarding the pulse shape of the inductive stimulation devices between biphasic full-wave stimulation (duration of the current pulse a full sine period) and biphasic half-wave stimulation. It is disadvantageous with the biphasic half-wave stimulation, however, that after the pulse, the voltage direction in the capacitor is inverted compared with the state prior to the pulse discharge, making the respective charging circuit more complex. Furthermore, in the biphasic half-wave stimulation, the direction of the magnetic field also changes, so that successive pulses create slightly different effects in the tissue.

The energy recovery in accordance with the circuits of FIG. 4 and FIG. 6 allows a reduction of the energy lost with each pulse and thus also of the power heat losses in the coil and the power electronics. This also allows the construction of repetitive inductive stimulation device, which can deliver up to 100 pulses per second. However, especially for this repetitive operation, energy consumption and coil heating is still considerable. In particular coil heating results from the very high coil currents required, being in the kilo ampere range.

Another way to reduce energy losses can be achieved by reducing current heat losses of the coil (R. Siebner, U. Ziemann, "Das TMS-Buch", Springer publishing house, ISBN-13 978-3-540-71904-5). This is done by increasing the effective conductor cross-section, in that, on the one hand, thicker conductor material can be used and, on the other hand, the conductor can be filamented with high-frequency wire, so that the current displacement effects in the conductor are reduced. However, the electrical resistance of the coil cannot be reduced arbitrarily for weight reasons.

As to the temporal course of the stimulus pulse, the three wave types mentioned, the damped monophasic pulse, the biphasic half-wave pulse and the biphasic full-wave pulse, still represent the only pulse shapes that are used in commercial inductive magnetic stimulation devices. All these wave shapes are ultimately based on the principle of the resonant oscillating circuit, wherein the coil is the inductor.

Therefore, the previously used devices also have the great disadvantage that the pulse duration depends on the inductance of the coil. In particular, for example, small coils often have design-related lower inductance than large coils; therefore, the pulse duration with previous systems could not be kept constant in an optimal range when using different coils.

Occasional experiments with other pulse shapes, as in Peterchev et al. 2008 with a rectangular shape (A. V. Peterchev, R. Jalinous, and S. H. Lisanby: A Transcranial Magnetic Stimulator Inducing Near-Rectangular Pulses With Controllable Pulse Width (cTMS), IEEE Transactions on Biomedical Engineering, vol. 55, no. 1, 2008) are either very energy inefficient or they lead to highly complex technical structures and are therefore too expensive for commercial technical realization For all applications, the disadvantage, therefore, of inductive magnetic stimulation still is high energy consumption, very rapid overheating of the coil and high weight of the charging and pulse generating electronics.

Another disadvantage is that the temporal course of the stimulus pulse can not be individually flexibly adapted to certain nerve cell or axon types or other requirements.

OVERVIEW OF THE INVENTION

The object of the invention is to provide a method and a device for generating freely selectable or optimized magnetic pulses for the stimulation of nerve and/or muscle cells, by means of which the disadvantages mentioned are avoided.

This object is satisfied by a method for stimulation of nerve and/or muscle cells with magnetic field pulses having the features indicated by a device for generating magnetic field pulses via current pulses in a coil and by a computer-readable storage medium with instructions for determining an optimized temporal course of the current pulse. Advantageous embodiments of the invention are the subject matter of the dependent claims.

The invention is based, on the one hand, on the realization, that with improved adaptation of the temporal course of the fields and currents induced in the tissue to the dynamic charge transport phenomena of the nerve or muscle fibers, the required field strength and field energy for inductive stimulation of these fibers can be reduced. On the other hand, the present invention is based on the finding, that the temporal course of the stimulation pulse must be adaptable in a wide range in order to either be able to stimulate different cell types or to fulfill different optimization criteria. For this, in particular the associated power electronics are to change the temporal course of the brief magnetic field pulse generated by the coil compared with previous systems in such a manner, that non-sinusoidal pulses are generated with course shapes, like they result either as an optimized result of a numerical simulation of the membrane behavior or as a result of an optimizing experimental investigation of nerve cells.

In a preferred embodiment of the invention, magnetic field pulses with a selectable temporal course are generated, which cause electrical stimulation currents in the body tissue and thereby in turn trigger action potentials of nerve and/or muscle cells. The current necessary for generating the field pulses via a coil should be selectable from several possible shapes. In particular, these possible shapes should be externally predeterminable for the device, e.g. in the form of a data record. Preferably, pulse shapes should here be predeterminable, whose temporal course shape is optimized with respect to certain parameters.

In another embodiment, the temporal course of the current pulse is computed by means of an arithmetic method, which numerically maps the electrical behavior of nerve and/or muscle cells as well as the coil and optimizes the temporal course of the current pulse regarding at least one parameter.

In another embodiment, the temporal course of the current pulse is determined via the stimulation of the nerve and/or muscle cells with current pulses of a predetermined shape, where also here an optimization of the temporal course of the current pulse occurs regarding at least one parameter. Furthermore, essential parameters of the stimulated nerve and/or muscle cells are determined from this optimized current pulse.

For both of these embodiments, noise signals can be used as a current pulse of a predetermined shape for determining the temporal course of the current pulse by means of simulation of the nerve and/or muscle cells and these noise signals can be temporally synchronized to the triggered action potentials of nerve and/or muscle cells.

The mentioned optimization of the course shape can pertain to different technical-physical parameters that are required for triggering a stimulation; for example, this optimization can pertain to minimizing the required field energy, the coil loss energy, the required electric coil current, the required coil voltage, the maximum steepness of the coil voltage or the coil current or to the acoustic artifact of the coil.

In other words, the current pulses generated according to the invention by the power electronics for the coil should no longer have a sinusoidal or damped sinusoidal course, but be characterized such that the electric field induced by the coil has a temporal course fulfilling one of the optimization criteria mentioned while having the same stimulating effect.

Further embodiments of the invention therefore differ from circuits, which together with the coil and a capacitor form a damped oscillating circuit whose current profile is composed of parts of damped sine waves, whose transitions between these parts respectively occur either at zero crossovers or when reaching of maxima and minima of the current through the coil.

In this, the current heat losses $E_v$ can in particular be estimated via the temporal integral of the square of the coil current $I_{sp}$ over the pulse duration $\tau$ multiplied with the internal resistance $R_i$ of the coil:

$$E_v = \int_\tau I_{sp}^2 \cdot R_i \cdot dt$$

The required maximum strength of the magnetic field can—for an unchanged coil—be estimated via the maximum coil current.

Furthermore, the power electronics for generating the current pulses in the coil should preferably be designed such that the high necessary electrical power for generating the magnetic field of the stimulation coil can be obtained from energy storage devices (e.g. capacitors) in order to achieve a uniform load for the power grid and, that furthermore most of this field energy of the coil can again be returned to these energy storage devices.

In this, this power electronics can preferably be designed such that the coil is controlled by means of a pulse width modulated signal (PWM signal) of a power converter, where the individual pulses of this PWM signal are to be substantially shorter than the entire pulse used for stimulating the nerves, so that the coil current can be controlled by the pulse width of this PWM signal. By controlling the temporal course of the coil current, the electric field induced in the body tissue can be respectively controlled. This allows the temporal course of the field induced in the tissue to adapted to the dynamic charge transport phenomena of the nerve fibers such that the optimization criteria mentioned are fulfilled.

The concept of the modular multilevel converter can be used as the current converter. This current converter is constructed of several individual modules controllable independently of each other, which are each constructed of power MOSFETs and a separate storage capacitor. The field energy of the coil required for the generation can therefore be gained from all capacitors of these modules. Furthermore, the field energy of the coil can accordingly also be fed back into the capacitors. Each individual module has two power connectors, and can each be charged and discharged in either polarization direction in the PWM mode.

One advantage of using the modular multilevel converter is that it is possible, by appropriate circuitry in the entire power converter, to deliver high pulse voltages at the stimulation coil while having low supply voltages of the individual modules.

A further advantage of using the modular multilevel converter is that the coil voltage can be controlled not only via the duty cycle of the PWM signal but also via the voltage and the number of currently active individual modules.

A further advantage of using the modular multilevel converter is that by asynchronously controlling the individual modules, the output signal of the current converter provides much finer time stepping of the PWM signal than the time stepping of a single module or an alternatively used current converter.

In particular, the voltage of each individual module can be reduced even further by using many modules connected in series when realizing the modular multilevel converter as the current converter for generating the coil pulses. Therefore, electronic components (e.g. power transistors and storage capacitors) with relatively lower electric strength can be used in these modules.

Furthermore, between the power electronics and the coil, an appropriate smoothing circuit can preferably be inserted, which smoothes the curve of the coil voltage and the coil current with respect to the PWM signal.

An advantage of the present invention is to provide a device and a method for inductive nerve stimulation requiring comparatively low field energy and field strength for stimulating the nerves. With this reduction of energy, the one or more capacitors used for intermediate storage of the pulse energy can also be reduced regarding their constructional sizes.

An advantage of the present invention is to provide a device and a method for inductive nerve stimulation which by the reduction of the necessary field energy requires a comparatively low coil voltage for the stimulation of the nerves, so that isolation spacing in the power circuit can be reduced and necessary safety measures can be simplified.

Power circuit is here understood as being the electrical circuit portion of a device for generating magnetic field pulses, in which the currents and voltages for the pulse are generated.

A further advantage of the present invention is to provide a device and a method for inductive nerve stimulation requiring a comparatively low coil current for triggering the stimulation. In this manner, firstly, current heat losses in the coil and in the supply leads can be reduced, secondly, electronic power components of comparatively lower current carrying capacity and correspondingly smaller constructional size can be used in the power circuit for generating the pulse.

A further advantage of the present invention is to provide a device and a method for inductive nerve stimulation, which due to their comparatively low energy consumption are suitable predominantly for repetitive stimulation with pulse repetition rates from 10 to 1000 pulses per second. At the same time, the devices for pulse generation according to the invention can be made relatively small, light, and therefore portable, so that they are also suitable for mobile applications or in the home-care field.

Another advantage of the present invention is to provide a device and a method for efficiently generating virtually any freely selectable temporal courses of the magnetic field pulses at the same time having high performance and low losses. The pulses can in particular be shaped such that the temporal courses of the currents induced in the tissue are optimally adapted to the dynamic charge transport phenomena of the nerve fiber, thereby reducing the field strength and field energy required in the coil for the stimulation.

A further advantage of the present invention is, that using a power circuit for generating freely selectable current profiles for the coil pulse, also enables the same device to selectively deliver differently shaped pulses. In this manner, pulses can be generated which on the one hand can stimulate specific types of nerve cells. Furthermore, the pulses can again be shaped such that they cause a low noise level in the coil or that they have a maximum stimulating effect while disregarding the coil losses.

BRIEF DESCRIPTION OF THE DRAWINGS

The above-mentioned and other objects, features and advantages of the present invention become more apparent from the following detailed description in combination with the accompanying drawings, in which.

In the drawings, like reference numerals are to depict like parts, components and assemblies.

DETAILED DESCRIPTION OF PREFERRED EMBODIMENTS

The invention is based on the finding that certain technical-physical parameters, which are required for the stimulation of nerve and muscle tissue, can be reduced significantly for inductive stimulation if the temporal course of the electric field induced in the body and the resulting currents are adapted to the dynamic behavior of ion transport in the nerve cell membrane. These parameters can, for example, be the required field energy, the coil loss energy, the required electric coil current, the required coil voltage, the maximum steepness of the coil voltage or the coil current, or the acoustic artifact of the coil.

Furthermore, the invention is based on the finding that the respective inductive stimulation devices must be able to generate different temporal courses of the current and the voltage during pulse delivery, in order to thereby fulfill the conditions for different optimization criteria.

Figure 8:
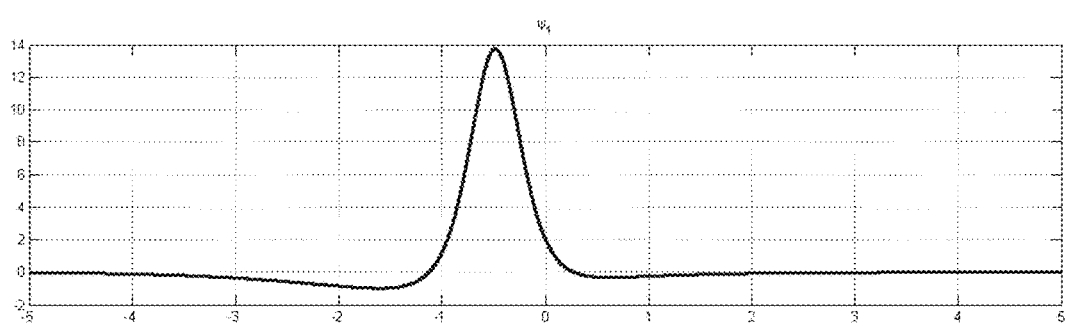
FIG. 8 shows by way of example an optimized temporal course of the necessary current at a cell membrane (and thereby also the curve of the coil voltage) during a stimulation pulse, as it is obtained as the optimized result of nerve cell modeling.

FIG. 8 by way of example shows a very favorable temporal course of the current for the excitation of a nerve cell that makes it possible to trigger an action potential having a low amplitude or stimulus energy. In particular, the first negative partial oscillation with a low amplitude—visible in FIG. 8—prior to the actual positive stimulation impulse, can significantly reduce the amplitude of the required current necessary for the stimulation by its excitation of dynamic processes at the membrane level. This means for example, that when the associated power electronics generate a temporal course of the pulse such that the coil voltage and thereby also the electric field induced in the body have a curve, as is shown in FIG. 8, then the required stimulus energy can be reduced.

The finding regarding the necessary temporal course shapes of the field is based on the mathematical modeling of nerve cells, as they were first established by Hodgkin and Huxley ((A. L. Hodgkin, A. F. Huxley: A Quantitative Description of Membrane Current and its Application to Conduction and Excitation in Nerve. Journal of Physiology. 117, 1952, p. 500-544). The model is based on a set of non-linear differential equations and simulates the behavior of nerve cells, in particular the behavior of short membrane segments of axons. With this model, for example, the reaction of an axon to electrical currents acting from outside can be comprehended. Therefore, the required stimulation currents can thereby be computationally determined at various temporal courses of the pulses that are required to trigger an action potential in the nerve cell.

In this, the model incorporates the dynamic non-linear behavior for example of sodium and potassium ion channels in the cell membrane into the simulation. Such models describe the temporal behavior of neurons in non-linear terms of high order and in particular can also simulate the triggering of action potential by a current pulse of different shapes applied from the outside. A direct inversion of the equations for simple determination of optimal pulse shapes is generally not possible. Optimization of pulse shapes must therefore be performed by skillful estimation with subsequent quantitative confirmation in the forward model. Furthermore, an accurate simulation of a triggering operation of the depolarization, during the short time period in which the external stimulating field acts, requires modifications and extensions of the previous models. For this, the active nerve models must preferably be extended by the electrical properties of the immediately surrounding tissue and by further ion channel modifications, as well as by the electrical properties of the coil. However, by comparison of the simulation and the experiment, it can be shown, that a realistic simulation of this axonal behavior is indeed possible.

In particular in relation to the sodium ion channels, it can be concluded from such a model that there exists both a channeling mechanism promoting the triggering of an action potential, as well as an inhibitory mechanism which rather suppresses triggering. These two mechanisms have a very different temporal behavior, which can be made use of for optimizing energetically particularly effective stimuli. It can in particular from the mathematical perspective to these mechanisms be concluded that the amplitude of the current pulse required for stimulation can for example be lowered, if the actual stimulation pulse is preceded by a partial oscillation with a low amplitude and opposite polarity in order to weaken the inhibitory mechanism. In this manner, dynamic processes on a membrane level can be exited such that the amplitude of the stimulation pulse required for a stimulation, and thereby also the required pulse energy, as well as the current heat losses in the coil can be reduced significantly.

Furthermore, in particular any optimization of the pulse shape (e.g. to a minimum required pulse amplitude or energy) is extremely complex due to the large number of variable parameters. In addition, it can further be distinguished for such a pulse shape optimization in terms of the parameters defining the pulse shape, whether the stimulation pulses to be examined are in sections sinusoidal or not. In particular stimulation pulses being sinusoidal in sections are much easier to simulate and to optimize since few parameters need to be changed. Furthermore, such signals being sinusoidal in sections can also still be generated technically relatively easily by a combination of resonant oscillating circuits. This is explained in the patent application submitted under the official file number 10 2009 023 855.7.

Figure 9:
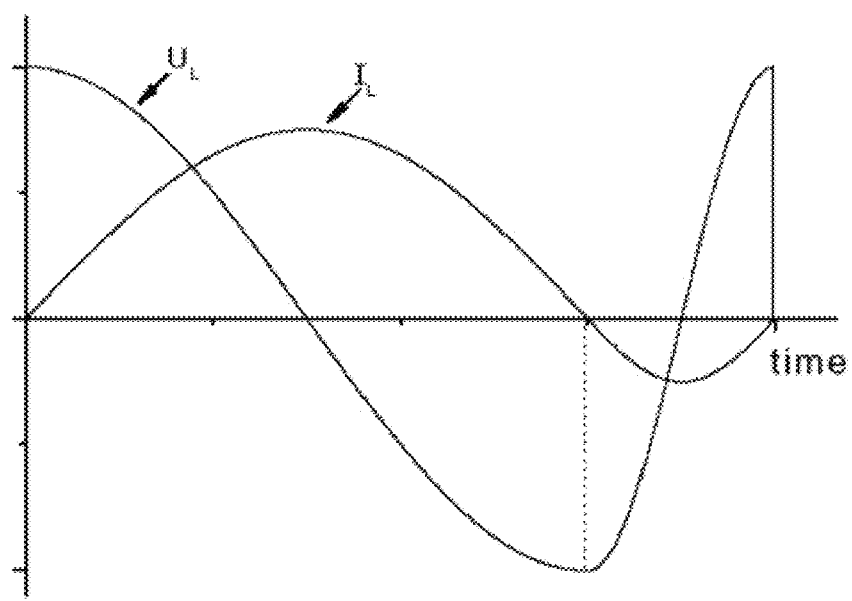
FIG. 9 shows a current pulse shape, which is composed of two sine half-waves of different frequencies.

FIG. 9 shows the curve of the electric current for a stimulus pulse induced in the tissue, which is composed of two sine half-waves of different frequency strung together.

Figure 10:
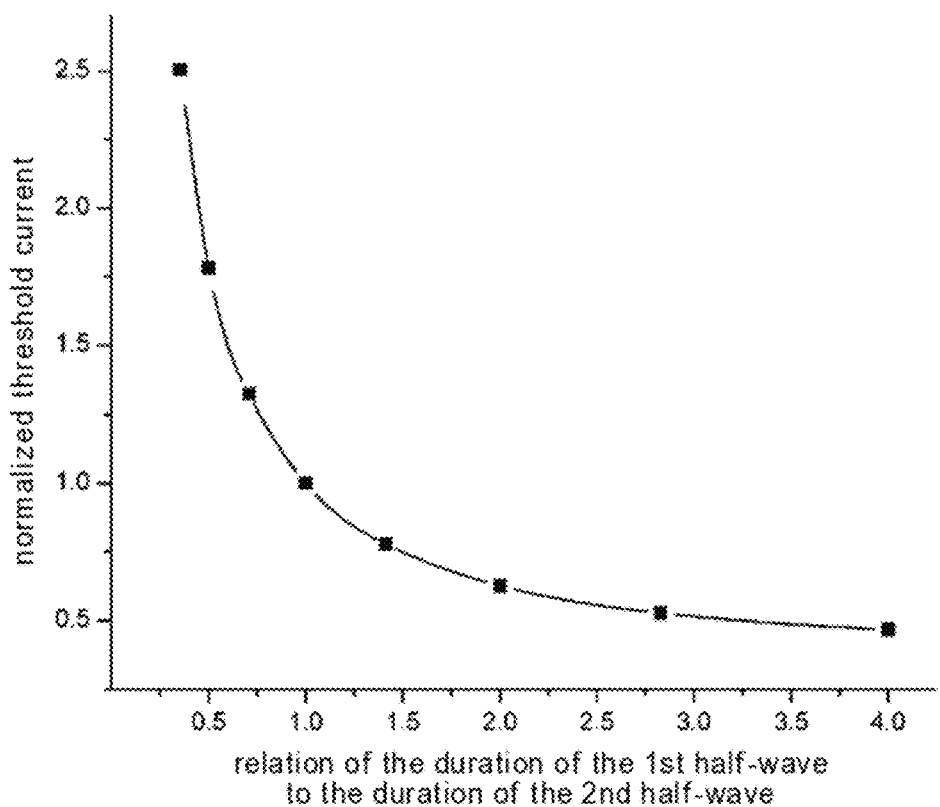
FIG. 10 shows the change in the threshold for triggering a nerve fiber in dependency of the quotient of the frequencies of two half-waves of different frequencies according to FIG. 9 strung together.

FIG. 10 shows an efficiency view of such pulses according to FIG. 9, in dependency of the frequency relation of the first half-wave to the second half-wave. In this, the total pulse duration was kept constant. The current amplitude was normalized—corresponding to a sine full-wave as a pulse shape—to a quotient of one. It is clearly visible that the threshold current necessary for a depolarization of the nerves decreases when the duration of the first half-wave is increased significantly relative to the second half-wave, as exemplified in FIG. 9. Therefore, by means of this modification of the pulse shape, significant energy optimization can already be achieved compared to previous commercial inductive stimulation system.

However, a more detailed analysis of stimulation pulses with a non-periodic and non-sinusoidal curve enables a completely free definition of the pulse with yet-again clearly enhanced optimization potential. It can there be shown, that pulses with several polarity changes of the coil voltage and thus of the induced field, as well as with a transient response, beginning with an initially low amplitude, enable yet another distinct reduction of the required pulse energy. For this reason, a method for the determination of suitable optimized pulse shapes, as is to be used according to the invention, was developed based on a simulation process. In this, the entire stimulation environment, including the stimulator and an individual nerve were recorded in a computer simulation model.

Figure 11:
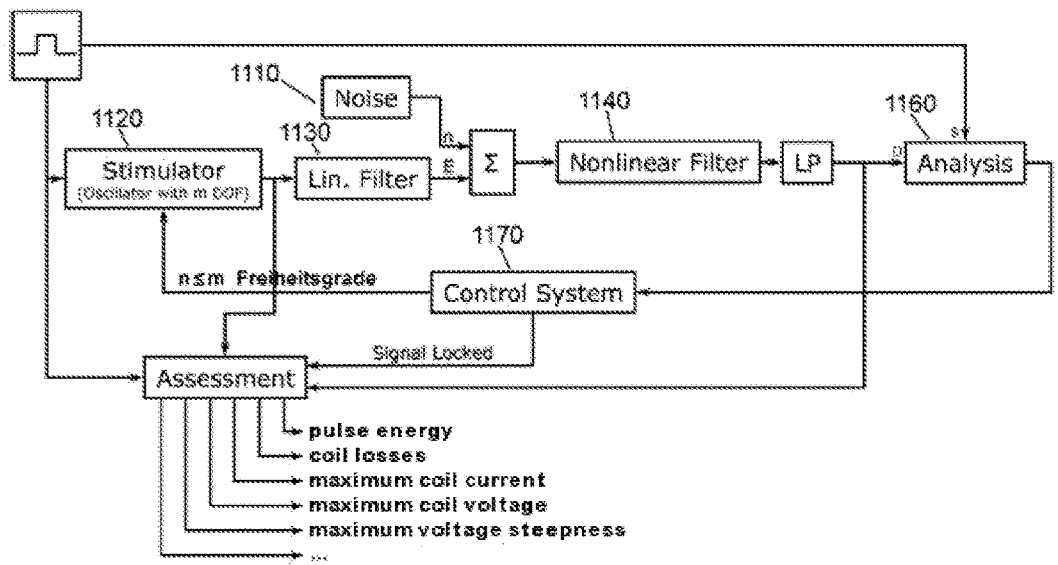
FIG. 11 by way of example shows a block diagram as it can be used for simulation of a stimulation environment for determining optimal pulse shapes.

FIG. 11 shows a block diagram with the respective components as can be used for the simulation of a stimulation environment for determining optimal pulse shapes, where these pulse shapes are generated by preferred embodiments. Basis of such a nerve simulation can for example be a mammalian axon. The control system for the simulation 1170 can for optimizing the pulse shape be used according to different criteria, such as minimization of a parameter or the maintaining constant of a reaction for a parameterized run of the stimulation system. In this, the simulation of the stimulator 1120 can, for example, be calibrated to a conventional stimulation system, so that this can provide good estimates, for example, the thermal behavior of stimulation coils when using different pulse shapes In contrast to previous work in this field, the realistic, non-linear nerve model of a mammal was preferred to the previously underlying linear approximations of the nerve membrane behavior, which is based on the dynamic description of the voltage-controlled channel proteins. This model is therefore much better suited to analyze the active process of stimulus generation. In particular, only by applying an active nerve model can the co-action of the voltage-controlled channels for triggering action potentials be taken into account, so that in this manner, even more clearly founded pulse shape optimizations result than with passive models.

Furthermore, in FIG. 11, the entire system for nerve and muscle stimulation is implemented, possibly reduced to m degrees of freedom for reducing complexity. Involved linear effects such as the induction in the target tissue can be described by numeric methods such as the finite element method or for simplification reasons, also by analytical formulations. In this block diagram, they are summarized in the block Linear Filter 1130. These filtered stimulation signals act, possibly together with noise processes 1110 as contained in the body and also in its environment, in the tissue upon the stimulation object which is shown in the block Nonlinear Filter 1140 with its entire non-linear dynamic and coupling-in mechanism regarding the induced stimulus. In this, a representation as accurate as possible of the desired stimulation object can very specifically be resorted to. For example, if an alpha neuron in the Nervus Medianus bundle is to be stimulated, then the nonlinear description of a respective axon can here be inserted. The reaction thereof can then be consulted both for the control settings in the Control System 1170 as well as for analysis 1160 of the stimulator settings and properties.

The following is to describe, with which mathematical methods an optimal temporal course of the stimulation pulse can be determined according to the optimization parameters:

Correlation Methods

The aim of this method is based on being able to map its behavior by an approximation using test measurements, with sufficient accuracy for the intended purpose, without detailed knowledge of a non-linear dynamic system.

Wiener-/Volterra Series Representation

Based on the work of N. Wiener and V. Volterra, for example, a series representation for a system can be illustrated taking the following or an equivalent form:

$$s(t) = a_0 + \sum_{i=1}^{\infty} \frac{1}{i!} \cdot \int \ldots \int a_i(\tau_1, \tau_2, \tau_3, \ldots, \tau_i) \cdot x(t-\tau_1)x(t-\tau_2)x(t-\tau_3) \ldots x(t-\tau_i)d\tau_1 d\tau_2 d\tau_3 \ldots d\tau_i$$

This is applicable both to individual parts as well as the overall system of the stimulator and the stimulated object. The quantity s (t) presently describes the neuronal response, x (t) the temporal course of the stimulation; for an overall system description, for example, the voltage curve at the stimulation coil. The parameters $a_j$ (core) are to be determined accordingly, such that they reflect the system as accurately as possible. Depending on the system and its convergency in this series representation, the development can already after a very limited number of summands be terminated in order to neglect higher terms. If one restricts the representation, for example, only to the zero$^{th}$ and first order with $a_0$ and $a_1$, then this corresponds to a linearization of the system around an appropriate operating point in a typical step response specification. The parameters can be determined in many ways from test measurements such that this ensemble of test stimuli can be best simulated.

As input signals for test or system analysis purposes, varying, stochastic or pseudo-stochastic methods can here very well be used which ultimately each produce a specific output signal in the model. This may for example be a noise process. If the parameters of the input signal (for example, the power density as a measure for the amplitude) are drawn on as a control variable for controlling properties of the response signal (for example, a certain average peak amplitude), the operating point of the series expansion can additionally be controlled.

As a result, a representation of the system is obtained, which in the form reduced to a few summands is significantly less complex than the original model representation. The sets of parameters $a_i$, on the one hand, characterize the entire system as well as the stimulation object more accurately and more sophisticatedly than any diagnostic procedures previously used in electrophysiology. In addition, simplifications can in this way also be found, that permit an inversion and thereby the estimation of the optimal input signal for a certain output reaction. This property in turn can be used as a program base for the new stimulation system.

Spike-Triggered Average, Spike-Triggered Covariance and Principal Component Analysis Another method for the characterization of parts or the overall system comprising a device and a stimulation target is to determine the so-called spike-triggered averages (STA). This can be done, for example, by stimulation with noise (optimally in white and Gaussian distribution). When such a stimulation signal triggers a reaction pulse, then the latter is used as a synchronization mark. If this process is repeated over a certain number of attempts, then all these stimuli with their respective synchronization marks can be formed to the STA by family averaging or summation, respectively, which thus provides a temporal course for a stimulation signal having characteristics which were inherent to all successful stimuli.

$$\varphi_{STA}(t) = \sum_i s_i(t - \tau_i)$$

In this, $s_i(t)$ are the stimuli and $\tau_i$ the synchronization marks defined by the response. Here, too, the operating point of this linearization can be influenced by controlling the stimulation process. For white Gaussian noise, this is done most easily via post-control of the distribution width $\sigma$, in order, for example, to obtain a specific rate of response signals or responses with a certain amplitude (for example, half the saturation maximum, or the like).

In order to obtain more information about the system, the stimuli synchronized with each other can also be subjected to a Karhunen-Loeve transformation or to a principal component analysis in the quantized case As a result, one obtains a set of eigenvectors and associated eigenvalues, which characterize the system at the operating point. If the operating point is located close to the trigger threshold of the corresponding nerve or muscle cell, then, for example, the eigenvector with the largest absolute eigenvalue specifies that component in a waveform, which for the same slight gain for the latter, entails the most influence on the reaction.

Accordingly, the eigenvectors for the next largest eigenvalues follow. These can also be used together in linear combinations.

As a variance measure to the STA, the spike-triggered covariance (STC) is suited for diagnosis. It represents the covariance matrix of the individual stimuli once the STA has been subtracted from it:

$$P_{s(t)}(\text{response}) = \frac{P(reponse)}{P(s(t))} P_{response}(s(t))$$

Optimization with a Constraint

Possible waveforms as they are to be generated by preferred embodiments of the invention can also be obtained from optimization algorithms that are applied to parts of the system or the entire structure. The object of the minimization can be technical parameters such as the field energy, the coil loss energy, the maximum of the amount of the required coil current, the maximum of the amount of the required coil voltage, the maximum of the amount of the temporal steepness of the coil voltage, or the coil current, required for a pulse Furthermore, the optimization can also relate to minimal tissue heating caused by induced currents, a maximal stimulation effect at a predetermined maximum value of the coil voltage or a smallest possible acoustic artifact of the coil, i.e. the perceived loudness of the coil during the pulse. From these optimizations mentioned, pulse shapes are to be determined, which achieve a respective identical stimulation result, like the triggering of action potentials.

In addition, also the greatest possible difference in sensitivity of several structures of cell tissue spatially close to each other can be determined for certain stimuli, in order to be able to perform an optimal selective stimulation of only one of these respective cell types.

In addition, for the stimulation and study of neurons in the brain, the use of an optimization algorithm for determining the necessary stimulation waveform is also of particular interest in order to obtain specific reactions with special properties. In this manner, for example, specific parameters for the optimal stimulation of certain diseased tissue structures can be determined, allowing for diseases in such tissue structures to be detected.

Under the constraint that a cellular response (for example, of certain strength) is excited for the individual stimulation object, a numerical optimization algorithm can determine the optimum waveform for the desired conditions for a corresponding model of the stimulation object and the stimulator. An example of this can be certain properties of the I-wave patterns of certain motor neurons of the motor cortex, which can be formulated accordingly in an objective function to be minimized and handed over to the algorithm with the model. On the one hand, local, mostly gradient-based operating algorithms are used for this, as well as global or pseudo-global seeking methods. The latter are often based on principles of mutation, inheritance and combination or swarm intelligence.

An electronic circuit according to the invention, which via a coil generates pulses with the above-described properties can therefore fulfill the respective above-described optimization objectives. For example, pulses can be generated which have a lower magnetic field strength and therefore require a lower field energy for triggering stimuli in comparison to previous systems for the inductive magnetic stimulation Accordingly, the required coil current and thus also the losses of the coil as well as the heating can, for example, thereby be reduced. By reducing the field energy, the coil voltage necessary for stimulation can furthermore be reduced. It is in particular advantageous, if the corresponding electronic circuit, in contrast to previous systems, is capable of selectively producing different pulse shapes for the coil.

Figure 1:
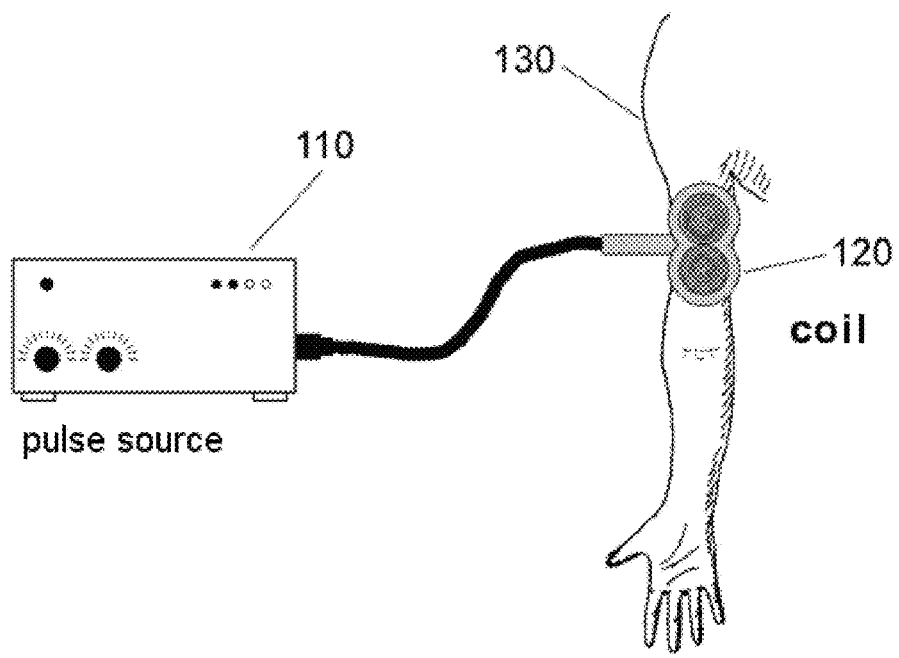
FIG. 1 shows a pulse source, the coil coupled via a cable, and the tissue structure to be stimulated (human upper arm)
Figure 2:
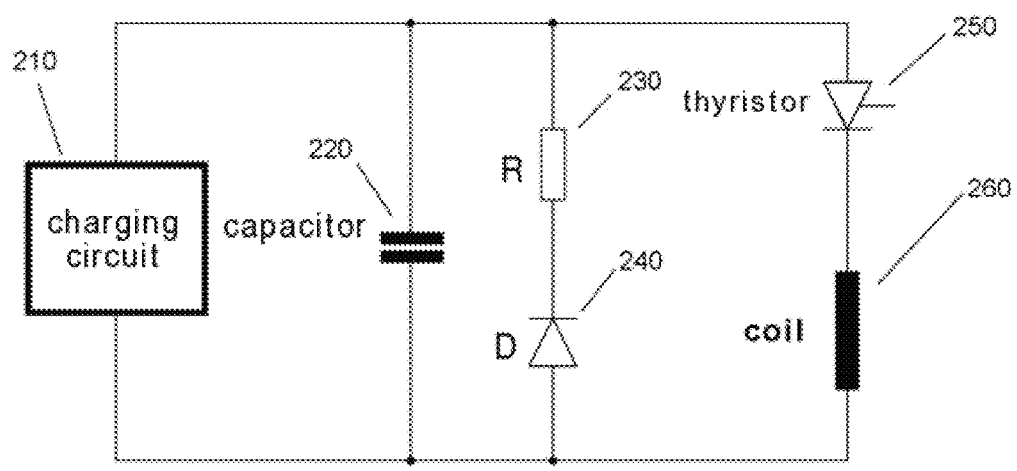
FIG. 2 shows the basic structure of a monophasic power circuit.
Figure 3:
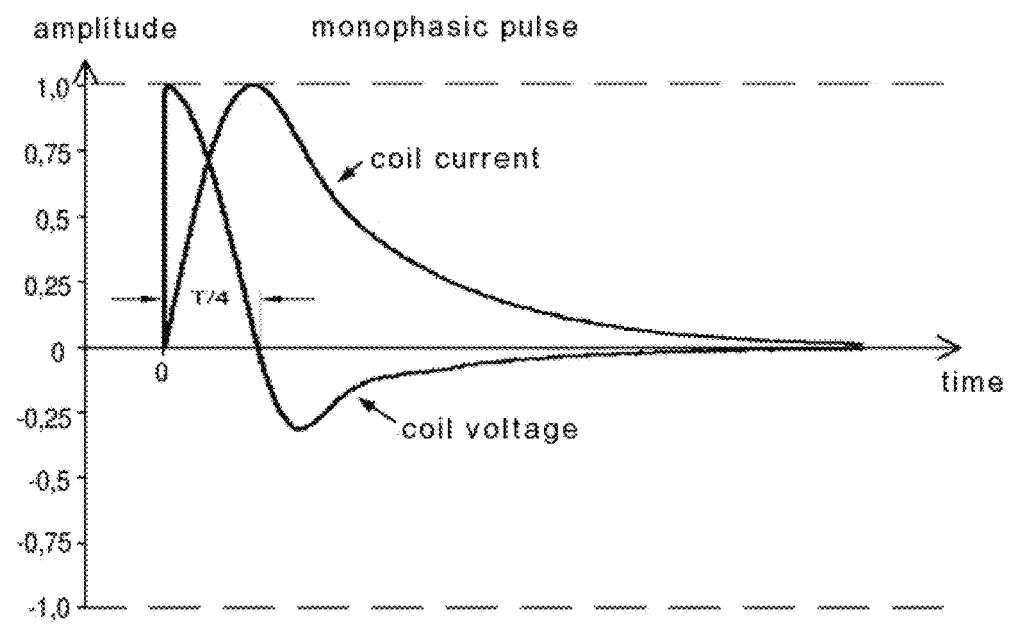
FIG. 3 shows the voltage curve and current profile in the coil of a monophasic stimulator during a pulse.
Figure 4:
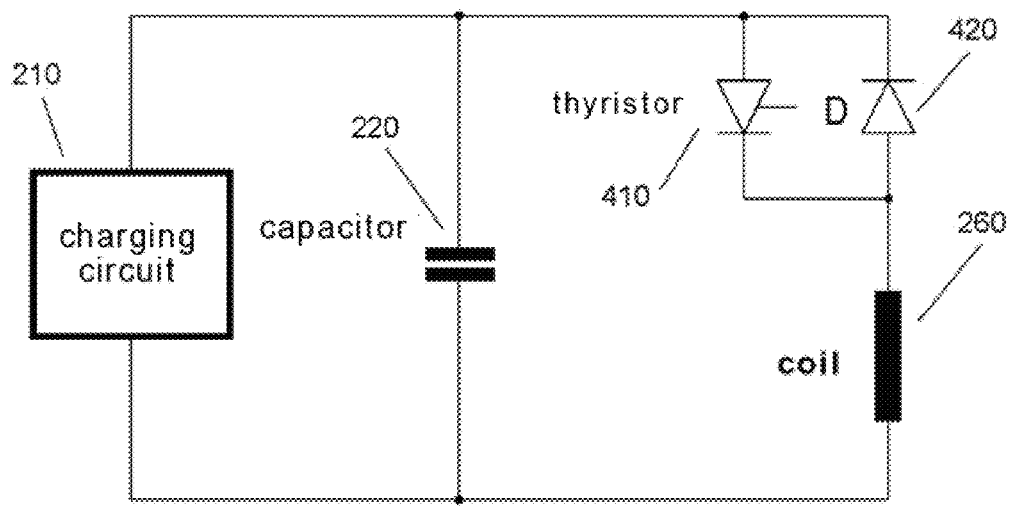
FIG. 4 shows the basic structure of a power circuit for generating sine full-waves.
Figure 5:
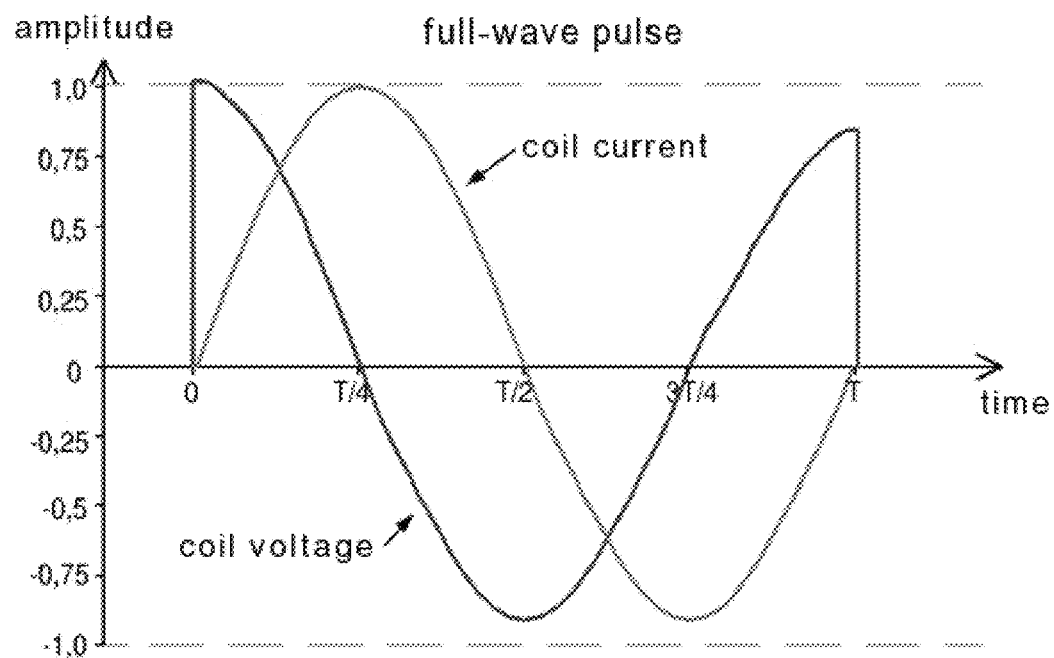
FIG. 5 shows the voltage curve and current profile of a full-wave stimulator in the coil during a pulse.
Figure 6:
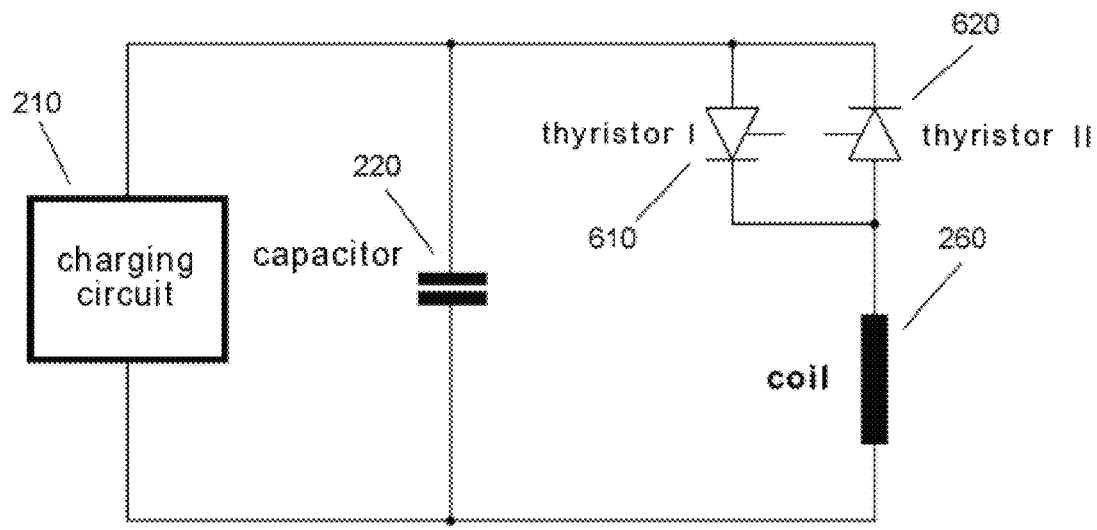
FIG. 6 shows the basic structure of a power circuit for generating sine half-waves.
Figure 7:
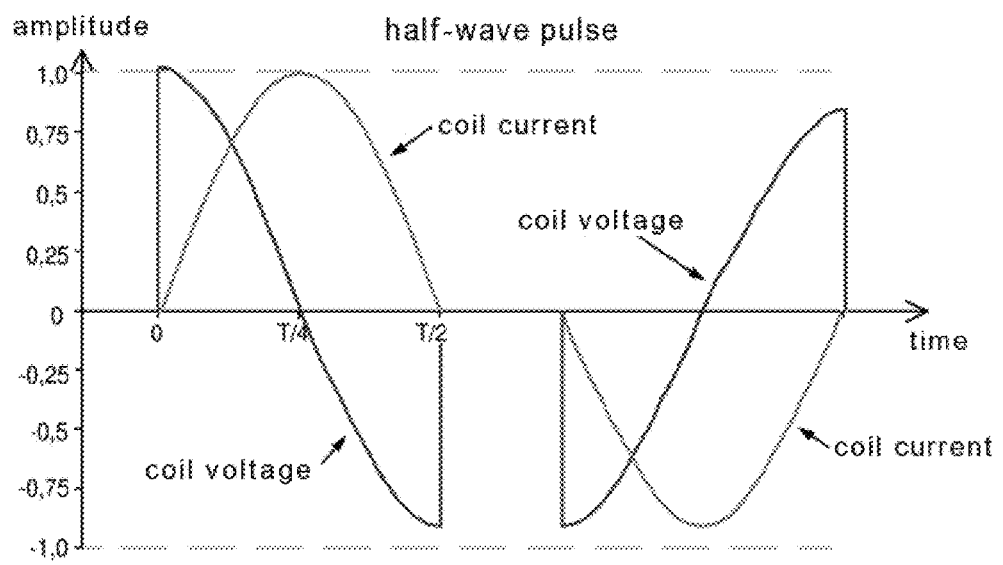
FIG. 7 shows the voltage curve and current profile of a half-wave stimulator in the coil during a pulse.

For the technical realization of such pulse shapes, however, a resonant circuit principle, such as is for example shown in FIG. 6, can no longer be used. Even coupling a plurality of oscillating circuits for generating a pulse signal composed of several sine partial oscillations would be technically too complex for generation of such pulse shapes due to the required high pulse power.

In principle, the required currents and voltages for the coil, as are required for nerve stimulation with such pulse shapes, could be generated according to the linear regulator principle. According to a preferred embodiment of the invention, arbitrary freely selectable courses of the coil current can therefore be generated via a sufficiently high supply voltage and a controllable electrical resistor connected to the coil. In this, power transistors can be used as controllable resistors. By using a ground potential which, for example, is disposed centrally between the positive and the negative terminal of this supply voltage, both positive as well as negative voltages can be generated in the coil. However, this linear regulator principle requires high-power, costly transistors as controllable resistors. Furthermore, returning field energy from the coil is only possible to a very limited extent.

In order to use the possibility of recovery of the magnetic field energy in a capacitor for non-sinusoidal pulse shapes, as they result from the above-described optimization, it is advantageous to use power converter technology for this. Power converters are semiconductor-based circuits of power electronics that operate according to the PWM principle. This means, these circuits are based on very rapidly switching on and off a respective voltage source, where the current profile can additionally be smoothed by the inductance of a coil. By appropriate time patterns and the use of multiphase systems, and by so-called multi-quadrant operation, the conversion of direct current and alternating current to almost any value of current and voltage can be possible in this manner. In particular, such a converter can arbitrarily send electrical power between two consumers/producers back and forth between these two components.

In a preferred embodiment of the invention, a power converter can therefore be used as a pulse source for the magnetic neurostimulation. The power converter can in the stimulation coil generate an almost freely selectable temporal current profile. In this, the stimulation coil by means of its inductance smoothes the current curve switched by the power converter. At the same time, the electrical energy can by means of this circuit principle be sent from one or more storage capacitors to the coil and back again, so that the magnetic field energy of the coil can for the most part be recovered.

Figure 12:
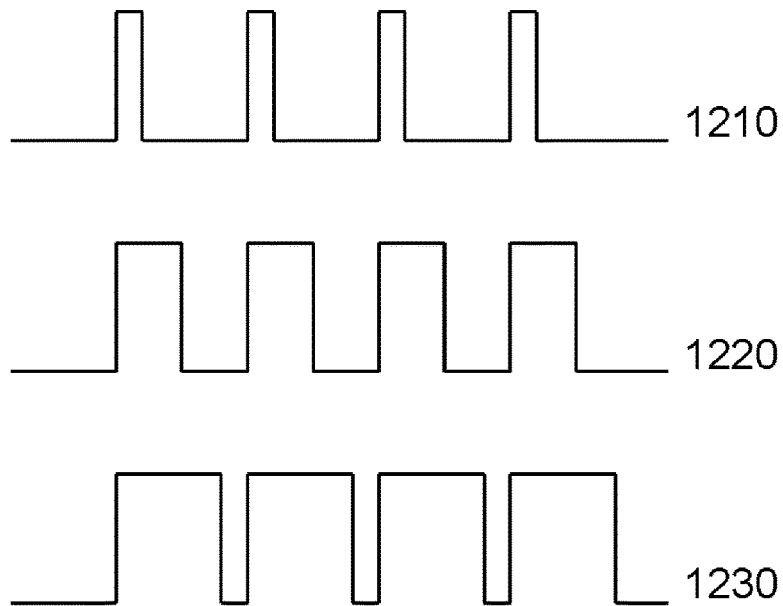
FIG. 12 by way of example shows output signals of a PWM current converter at different duty cycles.

FIG. 12 by way of example shows three output signals of a PWM converter 1210, 1220 and 1230 having the same clock frequency but differing duty cycle. In this, the mean value of the output signal increases from signal 1210 via 1220 to 1230. Given correspondingly low losses of the semiconductor switches, the mean value of the output voltage can be arbitrarily varied at very low losses.

Though conventional power converters are well developed in energy technology, they are little suited as a pulse source for optimized coil pulses in magnetic stimulation. This is partly because such systems are generally designed for continuous operation (for example, for generating periodic AC signals) and designed not for generating short-period pulses. Therefore, a respective high-performance power converter having a capacity of several megawatts would be required for a stimulation system. Such a power converter, however, would be too large and expensive to be used as a medical device. Another disadvantage of conventional power converter lies in the temporal resolution: To replicate a corresponding current profile of the coil pulse by PWM operation, the power converter must switch at a respectively high frequency; however, semiconductors with the required high current carrying capabilities usually have relatively long switching times, so that such a power converter could not be actuated fast enough to sufficiently accurately replicate the required temporal course of the pulses.

Furthermore, there was previously no reason apparent for the use of power converters for magnetic neurostimulation, since for pulse shape optimization, only extremely simple linear nerve models have to date been underlaid, which in turn presented no advantage for non-sinusoidal waveforms.

A modified concept of the modular multilevel converter (according to the published patent application DE 101 03 031 by R. Marquardt) has proven particularly advantageous as a power converter for optimized inductive magnetic stimulation. This current converter is comprised of several individual modules controllable independently of each other, which are each constructed of power semiconductors and storage capacitors. Each individual module has two power connectors, and can each be charged and discharged in either polarization direction in the PWM mode.

Figure 13:
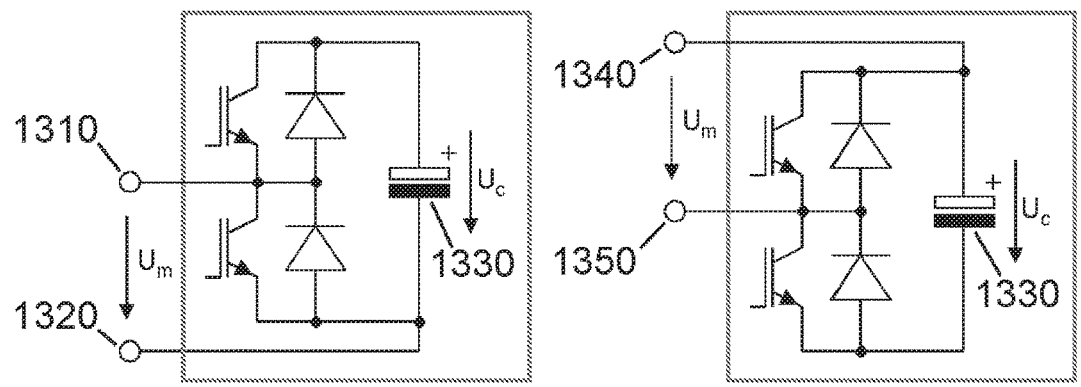
FIG. 13 by way of example shows two variants of a half-bridge module of a modular multilevel converter.

FIG. 13 shows two embodiments of half-bridge modules of a modular multilevel converter, such as can be used in preferred embodiments of the invention. By respectively actuating the semiconductor switch, the module can assume three possible states at its terminals 1310 and 1320 or 1350 and 1340, respectively: a switching state in which the terminal voltage of the module assumes the value zero independently of the terminal current direction (except for the passage voltage drop of real semiconductors), a switching state in which the terminal voltage of the module assumes values different from zero independently of the terminal current direction and the subsystem—depending on the terminal current direction—can receive regenerative energy from and deliver it to the storage capacitor 1330; and a switching state in which the terminal voltage of the module in dependency of the terminal current direction is directed such that the module does not deliver any energy.

Figure 14:
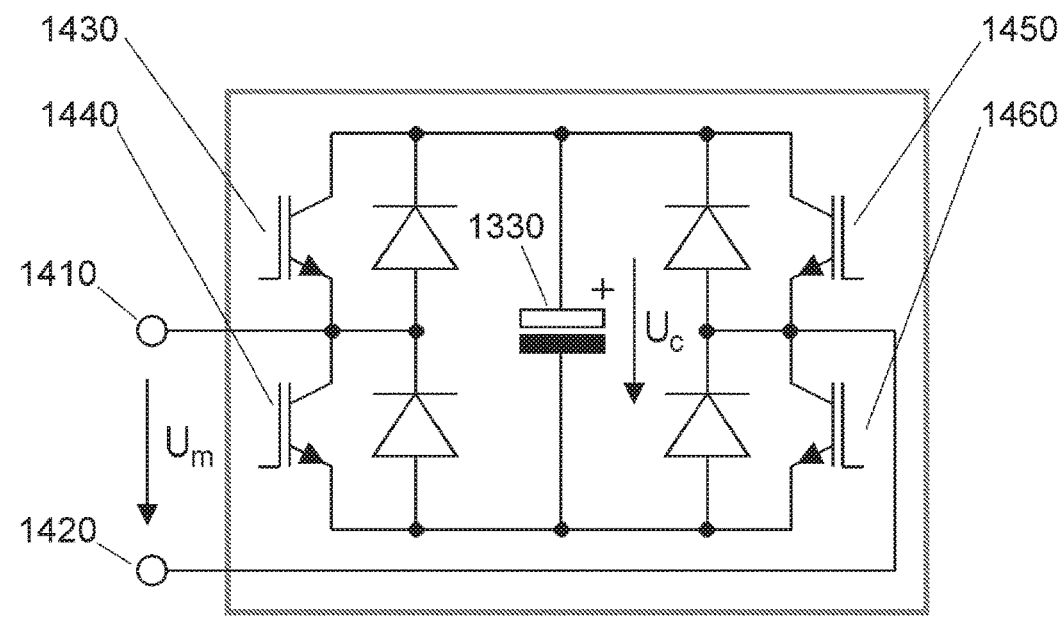
FIG. 14 by way of example shows a single full-bridge module of a modular multilevel converter.

FIG. 14 shows a single full-bridge module of a modular multilevel converter as it can be used in preferred embodiments of the invention. In contrast to the half-bridge modules, this module can also invert the terminal voltage, where even then, the polarity of the storage capacitor 1330 does not need to be inverted. Therefore, by appropriately actuating the semiconductor switches 1430, 1440, 1450 and 1460, this module can both during charging as well as during discharging of the capacitor 1330 process voltages and currents of both polarities (4-quadrant operation).

Figure 15:
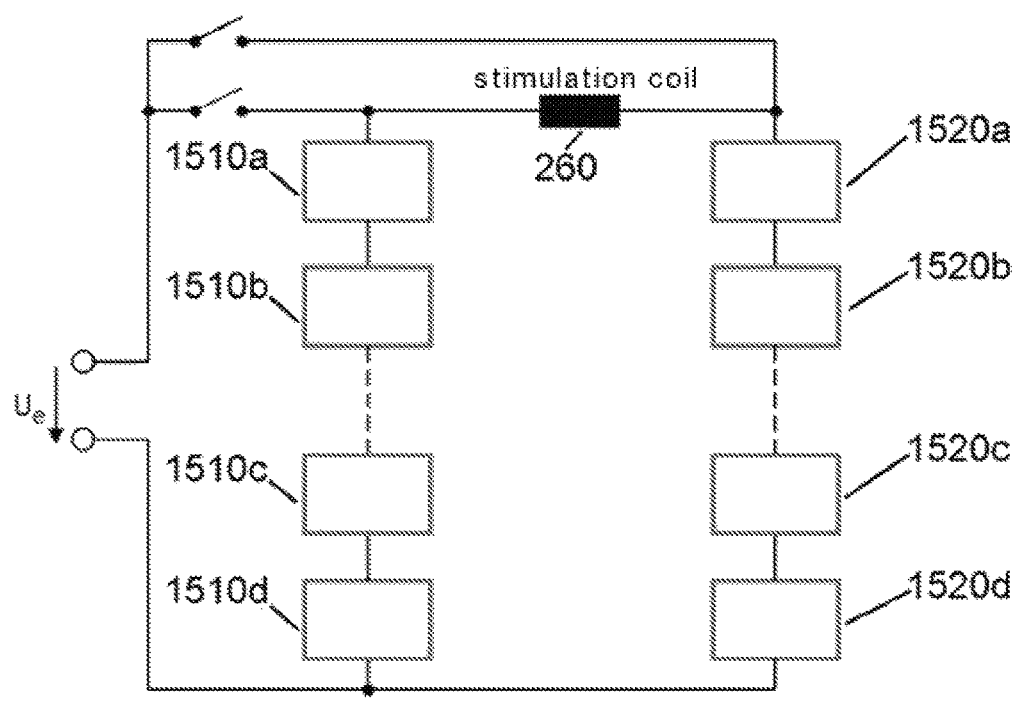
FIG. 15 by way of example shows an embodiment for the use of a modular multilevel converter for bipolar supply to the stimulation coil.
Figure 16:
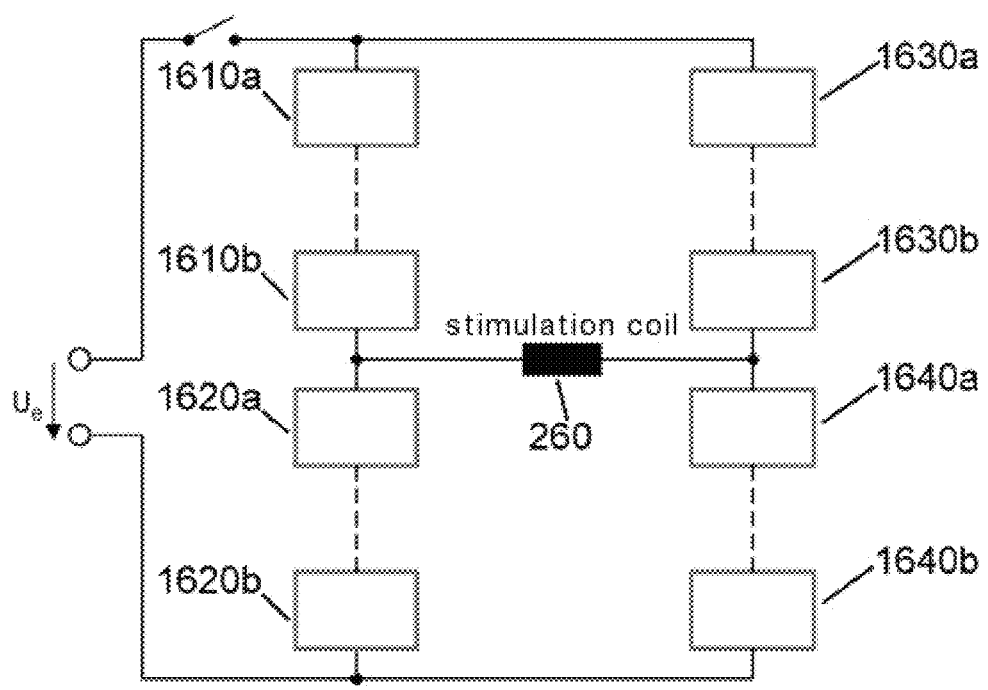
FIG. 16 by way of example shows another embodiment for the use of a modular multilevel converter for bipolar supply to the treatment coil.

FIGS. 15 and 16 show preferred embodiments of the invention using a modular multilevel converter using the example of a circuitry with a two-strand bipolar feed for the stimulation coil 260. All modules 1510a to 1640b and 1520d to 1610A can in the multiplex mode be charged with a low supply voltage. Since, when using the full-bride mode according to FIG. 14, each module can invert its voltage polarity by respectively actuating the module transistors, each strand must be able to produce only half the peak voltage.

The use of this power converter system based on the modular multilevel converter comprises the following advantages important for the realization of a pulse source of an inductive stimulator:

By using appropriately dimensioned capacitors in each individual module, the power converter itself can provide the necessary short-term energy storage to relieve the mains power supply in the form of capacitors 1330. These capacitors can therefore replace the large pulse capacitor 220 of previous devices for inductive neurostimulation.

By using a multitude of modules connected in series, there is only a relatively low voltage in each individual module, so that low-cost capacitors and semiconductor components can be used. In particular, especially efficient MOSFET transistors can presently be used having relatively low electric strength, very short switching times and very low conduction loss.

The use of MOSFET transistors as switching components in turn enables a design of the power converter for short-term current and power peaks (during the pulse phase), since these components can be acted upon by much higher currents than during continuous operation. Therefore, such a power converter can be designed having smaller, less expensive semiconductor components than a converter which is designed for continuous operation. Another advantage of using MOSFET transistors is, that these components can be relatively easily switched in parallel. This can achieve, by means of parallel connection allowing for the use of many relatively inexpensive MOSFET transistors from the field of consumer electronics, that the high currents necessary for the coil can be switched.

Since there is only one voltage direction within the modules, small, inexpensive electrolytic capacitors of very small size can also be used in these modules—in contrast to conventional resonant pulse sources for the magnetic stimulation—thereby enabling reduction of the constructional size of the pulse source.

The output voltage and hence the coil voltage can be controlled in the modular multilevel converter not only via the duty cycle of the PWM signal, but also via the voltage and the number of presently active individual modules, since the voltages of the individual actively switched modules can be added or subtracted to an overall voltage at the coil. This in turn can create a much smoother curve of the coil voltage than when using only the PWM principle of conventional power converters.

By asynchronously switching the many individual modules of the modular multilevel converter, generation of an output signal with significantly finer temporal stepping can be achieved than with a pure PWM signal. Therefore, regarding the coil current, a much finer temporal resolution of the generated output signal can be achieved at the coil than with a conventional power converter.

Figure 17:
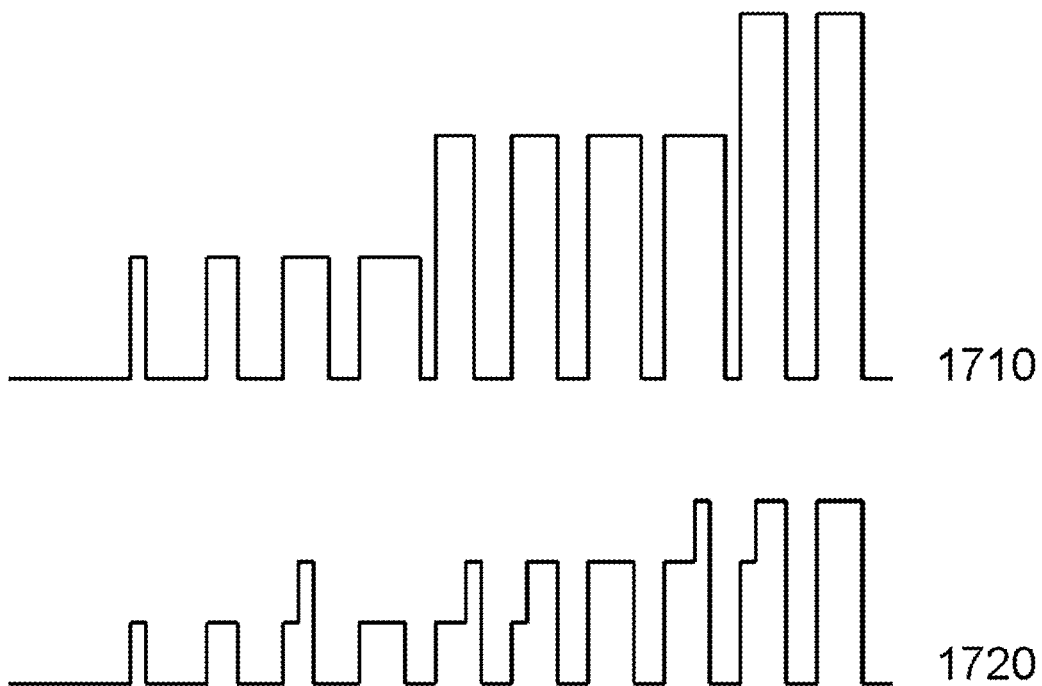
FIG. 17 by way of example shows PWM output signals of a modular multilevel converter with 3 voltage levels at various duty cycles, and FIG. 18 by way of example shows a smoothing circuit as it can be inserted between the output of a power converter and a stimulation coil, in order to smooth the curve of the coil voltage and the coil current with respect to the PWM signal.

FIG. 17 by way of example shows PWM output signal curves, such as can be generated at various duty cycles by a modular multilevel converter using a plurality of individual modules with a total of 3 voltage levels. At signal 1710, first one module, then two and finally three modules are synchronously switched one after another. At signal 1720, by way of example, three modules are asynchronously switched in order to obtain finer stepping.

Furthermore, in a preferred embodiment of the invention, a suitable smoothing circuit can be inserted between the power electronics for generating the coil pulse and the coil smoothing the curve of the coil voltage and the coil current with respect to a switched signal, e.g. a PWM signal.

Figure 18:
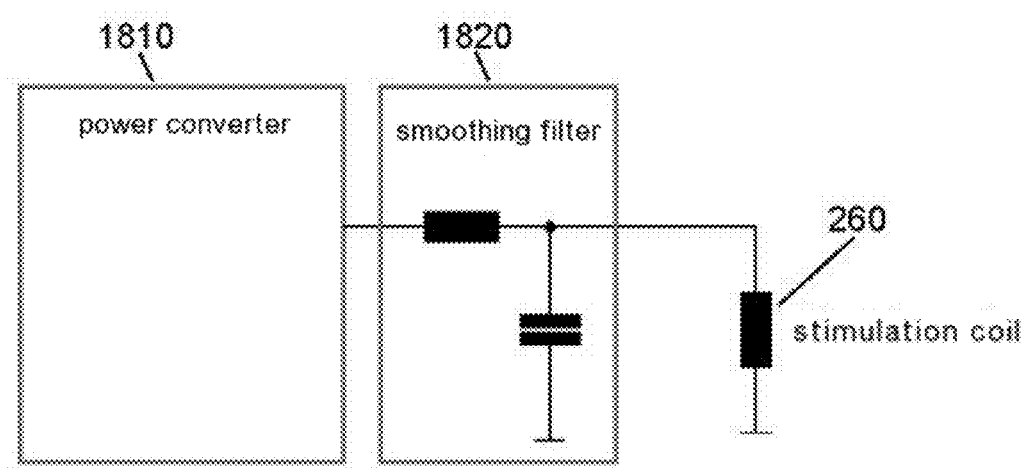

FIG. 18 by way of example shows a smoothing circuit which, for example, can be inserted as a low-pass filter between the output of a power converter 1820 and the stimulation coil 260, in order to smooth the curve of the coil voltage and the coil current with respect to the PWM signal.

Furthermore, in a preferred embodiment of the invention, the individual modules of the modular multilevel converter can be controlled such that a high pulse voltage can be delivered to the stimulation coil even with a low external supply voltage: In the charging mode, the modules of a strand can be switched by appropriate control of their respective power semiconductor such that, for example, only the capacitor of one module is connected with the external voltage supply and the remaining modules represent a direct short circuit connection to the outside. In this manner, the storage capacitors of the individual modules can be sequentially charged. In this manner, the overall system can be supplied and operated with a relatively low voltage. For delivery of the pulses at high voltages, the modules being connected in series can generate a voltage corresponding to the sum of their individual capacitor voltages. The expensive high voltage power supply required for previous devices for inductive neurostimulation can be dispensed with, whereby the constructional size of the pulse source can be reduced.

Therefore, the use of a power converter based on the concept of a modular multilevel converter in accordance with preferred embodiments enables saving many components of previous resonant power circuits.

In particular, the use of a power converter, as it was described, enables that magnetic pulses can be generated via a coil for the stimulation of cells with virtually any temporal course using a single device.

Therefore, the preferred embodiments of the invention are designed such that—selectable by the user—pulses of different shape are generated which satisfy the above-described respective optimization criteria.

In another preferred embodiment, optimized pulses are generated such that they optimally stimulate preferably very specific types of nerve or muscle cells. By adapting the shape of the pulses specifically to certain types of nerve and/or muscle cells, these nerve cells can be stimulated with the lowest possible stimulation threshold in preference over other types of nerve and/or muscle cells.

In another preferred embodiment, pulses can be delivered to the coil with an arbitrarily selectable temporal course. The temporal course of the coil current or the coil voltage can be read in from the pulse source either directly as an analog signal or in the form of digital data.

Furthermore, in a preferred embodiment of the invention, the use of a power converter, as it was describe, allows that pulses having a low noise level in the coil can also be delivered via the same device. Since the magnetic forces of the coil conductor during the pulse result in a short-term distortion of the coil, these distortions to some extent become noticeable as a very loud clicking noise. This so-called acoustic artifact of the magnetic stimulation can significantly disturb neurological examinations. For example, pulses having a small portion of high frequencies show a significantly lower acoustic artifact; however, these pulses require more energy for the same effect, so that the coil heats up faster. Previous devices that can only deliver a fixed pulse shape were therefore not able to be optimized to the lowest possible audible artifact.

Furthermore, in a preferred embodiment of the invention, the use of a power converter, as it was describe, allows that pulses having as high a stimulating effect as possible at a given maximum voltage can alternatively be delivered via the same device. The optimization described in terms of efficiency of the pulses indeed has the consequence, that the pulses at a given stimulating effect consume as little energy as possible; however, this does not mean that such pulses at a predetermined maximum amplitude of the coil voltage also result in maximum stimulation.

A further advantage resulting from the use of a power converter for generating the pulses for the coil lies in the fact that—contrary to the previously used inductive stimulation devices—the shape of the pulse is independent of the inductance of the coil used.

By appropriately clever embodiments, such as the use of rectifying circuit elements, like diodes in the single modules in FIGS. 13 and 14, problems arising in unknown stimulation coils from previously unknown electrical properties and their influence on the pulse shape can furthermore easily be solved by using another switching state. Energy still present at the end of a pulse in the magnetic field of the coil for above-mentioned reason can, for example, in this manner without further knowledge of the coil inductance be selectively depleted without danger, in that a passive voltage curve of almost any curve shape is predetermined, the polarity of which, however, is either—in the case of the diodes—not predetermined or, for example, is conditioned by controlling the coil current or its time derivative, respectively. This defines the power flow subject to strictly defined other degrees of freedom, which can therefore, for example, be forced back into the storage elements of the modules without causing uncontrolled discharge or conversion into heat. Knowledge of the last current profile, the inductance or loss resistances are in the simplest case not absolutely necessary for this. For the possible voltage curve and its representation, for example, by means of pulse width modulation, basically the same ancillary conditions are valid as for the active polarity-defining operation. In the embodiment via rectifying switching elements, the current flow automatically terminates as soon as all electromagnetic residual energy from the stimulating coil and other inductors is discharged.

An inverter-based stimulation system can in particular also be used for the optimization or analysis of certain pulse shapes directly at the target object, for example, at the brain or peripheral neurons. Either only a part, such as the neuron, or the entire system composed of the stimulator, the coil and the neuron can be considered to be the system to be analyzed. The input and output signal must be defined accordingly.

Unlike with previous devices for inductive nerve stimulation, a current-converter-based device is capable of generating the stimuli of different pulse shapes necessary therefor and of dynamically adapting the control method described above by way of example for determining optimal pulse shapes during operation. Likewise, the stimulator principle is able to generate noise signals To compensate for typical measurement errors and variances, where appropriate, the respective representation pair of input and output signals for the control algorithm should be physically measured several times and improved by averaging the signal-to-noise ratio.

The stimulator principle according to the invention, which is able to generate arbitrary pulse shapes, therefore also allows various examinations of nerve and muscle cells in electrophysiology and psychiatry. In contrast to examination methods such the analysis of the pure stimulation threshold or of the peripheral nerve conduction velocity (NCS, Nerve Conduction Study) and their changes, the above-described methods provide a full characterization of a neuron. In this manner, a much larger field of neural lesions can therefore very simply—after appropriate analyzes by means of different pulse shapes—be diagnostically characterized and classified by changing the respective parameters. Depending on the method, the nerve conduction velocity and the stimulation threshold are even without additional measurements directly calculable from the parameters.

Another field of application is the differentiated optimization of stimulator parameters (i.e., the temporal course of the pulse) directly at the object. This can take place directly on a person or done in advance in approximation for a variety of different stimulation objects so that they are then during the actual application available in a database and can be used accordingly. It is possible to adapt the pulse shapes not only to certain different cell types such as muscle cells or neurons or also to specific subtypes of the corresponding class, but also to parts of individual cells having electrically differing properties. With neurons, for example, dendrites, soma, axon and synapses are to be mentioned, which due to their different electrical behavior respectively require different pulse shapes for stimulation—for example, at an optimal low threshold. A system for determining an optimized pulse shape, based on the computational methods as described above, can in particular be advantageously integrated into the described stimulation device for generating arbitrary waveforms.

The use of magnetic pulses according to the method described can be used for stimulating nerve and muscle cells. In particular, a method according to the present invention can also be used for selective muscle formation or for representation of functional relationships of the neuromotoric system in humans and animals.

The duration of the magnetic field pulses delivered by the coil are approximately in the range of 20 to 3000 microseconds, preferably the duration should be in the range of 100 to 1000 microseconds The strength of the magnetic field pulses should at the coil surface be in the range of a flux density of 0.1 to 5 Tesla. Preferably, the magnetic flux density is in the range of 0.3 to 1 Tesla.

The invention claimed is:

1. Method for stimulating nerves or muscle cells, in which magnetic field pulses are generated which according to an electromagnetic induction principle induce stimulation currents in a body tissue triggering an action potential of the nerves or muscle cells, wherein said magnetic field pulses are generated by a coil which is positioned close to the body tissue to be stimulated such that said magnetic field pulses generated by said coil passes through the body tissue, and wherein said magnetic field pulses have a temporal course corresponding to a temporal course of a current through said coil and wherein the method comprises the following steps:
  adjusting one of several possible shapes of said temporal course of the current through said coil in a manner that said temporal course of said current through said coil is such that an electric field induced by said coil in said tissue results in a current whose temporal course is adapted to a dynamic charge transport phenomena of nerve fibers; and
  controlling said temporal course of said current through said coil according to an adjusted shape in order to generate said magnetic pulses via said coil in said tissue; and
  wherein at least two capacitors are used for storing and discharging the energy necessary for said magnetic field pulses and said capacitors can be differently connected to said coil via suitable switches such that different voltages arise at said coil and said temporal course of said coil current is approximated; and wherein for generating said temporal course of said coil current by means of connecting capacitors to said coil via switches, a modular multilevel converter comprising at least two half or full-bridge modules connected in series are used, where capacitors of said individual half or full-bridge modules of said modular multilevel converter are used as an energy storage for providing a stimulation pulse.

2. Method according to claim 1, wherein a voltage source of low voltage can be used for charging said modules connected in series of said modular multilevel converter, in that individual modules are connected with the energy source in short succession such that the respective modules presently not to be charged are switched such that they create a direct conductive connection between their power terminals.

3. Device for generating brief strong current pulses in a coil, such that said coil generates magnetic field pulses which according to an electromagnetic induction principle induce stimulation currents in body tissue triggering an action potential for stimulating nerve or muscle cells, wherein said coil is designed such that it is positionable close to said body tissue to be stimulated, so that a magnetic field generated by it passes through said body tissue, and wherein said device comprises at least one capacitor for storing and discharging the energy necessary for said magnetic field pulses and a suitable charging circuit for charging said at least one capacitor, and wherein said device comprises a power generating unit, which is arranged to generate a freely selectable temporal course of said current through said coil during said current pulse and wherein said temporal course of said current through said coil is controlled by the device such that an electric field induced by said coil in said tissue results in a current whose temporal course is adapted to a dynamic charge transport phenomena of nerve fibers; and where the at least one capacitor is used for storing and discharging the energy necessary for said magnetic field pulses and said at least one capacitor is selectively electrically connected via suitable power semiconductors to said coil such that different voltages arise at said coil and said temporal course of said current through said coil is achieved; and where by means of the electrical connection of the at least one capacitor to said coil by the suitable power semiconductors, a modular multilevel converter comprising at least two half or full-bridge modules connected in series is used for generating said temporal course of said current through said coil.

4. Device according to claim 3, where said at least one capacitor of individual half or full-bridge modules of said modular multilevel converter is used as energy storage for providing a stimulation pulse.

5. Method for stimulating nerves or muscle cells in which magnetic field pulses are generated which according to an electromagnetic induction principle induce stimulation currents in a body tissue triggering an action potential of the nerves or muscle cells, wherein said magnetic field pulses are generated by a coil which is positioned close to the body tissue to be stimulated such that said magnetic field pulses generated by said coil passes through the body tissue, and wherein said magnetic field pulses have a temporal course corresponding to a temporal course of a current through said coil and wherein the method comprises the following steps:

adjusting one of several possible shapes of said temporal course of the current through said coil in a manner that said temporal course of said current through said coil is such that an electric field induced by said coil in said tissue results in a current whose temporal course is adapted to a dynamic charge transport phenomena of nerve fibers, so that said temporal course of said current through said coil is optimized regarding at least one technical or physical parameter, and controlling said temporal course of said current through said coil according to an adjusted shape in order to generate said magnetic pulses via said coil in said tissue, wherein power semiconductors generating pulse-width-modulated signals are used for generating said temporal course of the current through said coil, and further wherein said power semiconductors generating pulse-width-modulated signals use multilevel converter modules for generating at least three voltage levels, and said multilevel converter modules are switched asynchronously, and wherein individual pulses of the pulse-width-modulated signals that are used to generate a corresponding magnetic field pulse are shorter than said corresponding magnetic field pulse.

6. Computer-readable non-transitory storage medium containing instructions executable by a processor for determining an optimized temporal course of a current pulse through a coil for stimulating nerve or muscle cells in body tissue according to a principle of electromagnetic induction, in which an induced electric field pulse generates currents in said tissue triggering action potentials of said nerve or muscle cells, where said coil is positioned close to said body tissue to be stimulated such that said magnetic field generated by said coil passes through said body tissue and where said current pulse through said coil generates a temporally changeable magnetic field passing through said body tissue thus inductively generating said electric field pulse in said body tissue, comprising:

computing the temporal course of said current pulse by means of a computing procedure which numerically maps the electrical behavior of nerve or muscle cells and the coil and optimizes said temporal course of said current pulse regarding at least one technical or physical parameter and wherein said temporal course of said current through said coil is controlled such that an electric field induced by said coil in said tissue results in a current whose temporal course is adapted to a dynamic charge transport phenomena of nerve fibers, wherein power semiconductors generating pulse-width-modulated signals are used for generating said temporal course of the current through said coil, wherein individual pulses of these pulse-width-modulated signals are shorter than an entire of said current pulses, and wherein said power semiconductors generating pulse-width-modulated signals use multilevel converter modules for generating at least three voltage levels and wherein further individual multilevel converter modules are switched asynchronously.

7. Device for generating brief strong current pulses in a coil, such that said coil generates magnetic field pulses which according to an electromagnetic induction principle induce stimulation currents in said body tissue triggering an action potential for stimulating nerve or muscle cells, wherein said coil is designed such that it is positionable close to said body tissue to be stimulated, so that a magnetic field generated by it passes through said body tissue;

wherein said device comprises at least one capacitor for storing and discharging the energy necessary for said magnetic field pulses and a suitable charging circuit for charging said at least one capacitor, and wherein said device comprises a power generating unit, which is arranged to generate a freely selectable temporal course of said current through said coil during said current pulse and wherein said temporal course of said current through said coil is controlled by the device such that an electric field induced by said coil in said tissue results in a current whose temporal course is adapted to a dynamic charge transport phenomena of nerve fibers, so that said temporal course of said current through said coil is optimized at least one technical or physical parameter, wherein power semiconductors generating pulse-width-modulated signals are used for generating said temporal course of the current through said coil and wherein individual pulses of the pulse-width-modulated signals that are used to generate a corresponding magnetic field pulse are shorter than said corresponding magnetic field pulse, further wherein said power semiconductors generating pulse-width-modulated signals use multilevel converter modules for generating at least three voltage levels and wherein further individual multilevel converter modules are switched asynchronously.

* * * * *